(12) United States Patent
Rilli

(10) Patent No.: US 10,441,142 B2
(45) Date of Patent: Oct. 15, 2019

(54) SEALING COMPONENT FOR AN ENDOSCOPE CONNECTOR

(71) Applicant: Digital Endoscopy GmbH, Friedberg (DE)

(72) Inventor: Christoph Rilli, Augsburg (DE)

(73) Assignee: DIGITAL ENDOSCOPY GMBH, Friedberg (DE)

( * ) Notice: Subject to any disclaimer, the term of this patent is extended or adjusted under 35 U.S.C. 154(b) by 0 days.

(21) Appl. No.: 14/906,257

(22) PCT Filed: Jul. 21, 2014

(86) PCT No.: PCT/EP2014/065587
§ 371 (c)(1),
(2) Date: Jan. 19, 2016

(87) PCT Pub. No.: WO2015/011075
PCT Pub. Date: Jan. 29, 2015

(65) Prior Publication Data
US 2016/0166131 A1    Jun. 16, 2016

(30) Foreign Application Priority Data
Jul. 22, 2013   (DE) ........................ 10 2013 214 278

(51) Int. Cl.
*A61B 1/04*   (2006.01)
*A61B 1/00*   (2006.01)
*A61B 1/12*   (2006.01)

(52) U.S. Cl.
CPC ........ *A61B 1/00137* (2013.01); *A61B 1/0014* (2013.01); *A61B 1/00062* (2013.01);
(Continued)

(58) Field of Classification Search
CPC ............ A61B 1/00114; A61B 1/00124; A61B 1/00137; A61B 1/0014; A61M 39/20
(Continued)

(56) References Cited

U.S. PATENT DOCUMENTS 3,549,806 A    12/1970 Wood
3,605,725 A    9/1971 Bentov
(Continued)

FOREIGN PATENT DOCUMENTS

CN    1286664 A    3/2001
CN    2762381 Y    3/2006
(Continued)

OTHER PUBLICATIONS

International Search Report dated Mar. 24, 2015 for International Application No. PCT/EP2014/075902.
(Continued)

*Primary Examiner* — Matthew J Kasztejna
(74) *Attorney, Agent, or Firm* — Knobbe Martens Olson & Bear, LLP (57) ABSTRACT

According to the present invention, there is provided a sealing component for an endoscope plug at an end of which a plug connection end to be sealed is arranged. The sealing component comprises: a body part having a blind hole-like endoscope plug insertion opening into which the plug connection end of the endoscope plug is sealingly insertable, and a fastening portion for the fastening at an endoscope cable of the endoscope whose endoscope plug comprises the plug connection end sealingly insertable into the blind hole-like endoscope plug insertion opening.

19 Claims, 3 Drawing Sheets

(52) U.S. Cl.
CPC ...... *A61B 1/00114* (2013.01); *A61B 1/00121* (2013.01); *A61B 1/00124* (2013.01); *A61B 1/121* (2013.01)

(58) Field of Classification Search
USPC .......................................... 600/132–133, 175
See application file for complete search history.

(56) References Cited

U.S. PATENT DOCUMENTS

| | | | | |
|---|---|---|---|---|
| 4,241,729 | A | * | 12/1980 | Aoshiro ............. A61B 1/00137 356/241.1 |
| 4,404,963 | A | * | 9/1983 | Kohri ................. A61B 1/00137 600/133 |
| 4,415,767 | A | | 11/1983 | Gill et al. |
| 4,670,009 | A | | 6/1987 | Bullock |
| 5,150,715 | A | * | 9/1992 | Ishiguro ................. A61B 1/018 600/463 |
| 5,245,133 | A | | 9/1993 | DeCarlo et al. |
| 5,569,157 | A | | 10/1996 | Nakazawa et al. |
| 5,588,950 | A | * | 12/1996 | Sano ........................ A61B 1/07 600/160 |
| 5,630,419 | A | | 5/1997 | Ranalletta |
| 6,383,132 | B1 | | 5/2002 | Wimmer |
| 6,547,722 | B1 | * | 4/2003 | Higuma ............. A61B 1/00096 600/133 |
| 6,582,361 | B2 | * | 6/2003 | Hirano ............... A61B 1/00137 600/132 |
| 6,716,160 | B2 | * | 4/2004 | Mitsumori ............. A61B 1/005 600/131 |
| 7,179,223 | B2 | * | 2/2007 | Motoki ............. A61B 1/00039 600/102 |
| 7,198,599 | B2 | * | 4/2007 | Goto ................. A61B 18/1492 600/104 |
| 7,841,880 | B2 | * | 11/2010 | Ikeda ................. A61B 1/00128 439/271 |
| 2001/0025135 | A1 | * | 9/2001 | Naito ................. A61B 1/00137 600/156 |
| 2002/0040180 | A1 | * | 4/2002 | Hirano ............... A61B 1/00137 600/132 |
| 2002/0115907 | A1 | | 8/2002 | Mitsumori |
| 2003/0092965 | A1 | | 5/2003 | Konomura |
| 2004/0015050 | A1 | * | 1/2004 | Goto ................. A61B 18/1492 600/104 |
| 2004/0143162 | A1 | * | 7/2004 | Krattiger ............ A61B 1/00096 600/175 |
| 2005/0004434 | A1 | | 1/2005 | Bob et al. |
| 2006/0116550 | A1 | * | 6/2006 | Noguchi ................. A61B 1/121 600/132 |
| 2006/0135851 | A1 | | 6/2006 | Yamazaki |
| 2006/0199999 | A1 | | 9/2006 | Ikeda |
| 2006/0252993 | A1 | * | 11/2006 | Freed ................... A61B 1/0052 600/146 |
| 2007/0106119 | A1 | * | 5/2007 | Hirata ................. A61B 1/00096 600/179 |
| 2007/0156018 | A1 | * | 7/2007 | Krauter ............. A61B 1/00142 600/102 |
| 2007/0221701 | A1 | | 9/2007 | Ortiz |
| 2007/0282371 | A1 | | 12/2007 | Lee |
| 2009/0209820 | A1 | | 8/2009 | Tanaka |
| 2009/0286412 | A1 | | 11/2009 | Ikeda |
| 2010/0168560 | A1 | | 7/2010 | Hauck et al. |
| 2011/0288372 | A1 | | 11/2011 | Petersen |
| 2011/0313252 | A1 | | 12/2011 | Lin |
| 2012/0170767 | A1 | | 7/2012 | Astrom et al. |
| 2012/0209068 | A1 | * | 8/2012 | Hosaka ............. G02B 23/2476 600/109 |
| 2014/0148646 | A1 | | 5/2014 | Inada |
| 2015/0057537 | A1 | | 2/2015 | Dillon et al. |
| 2015/0173711 | A1 | | 6/2015 | Hiraoka |

FOREIGN PATENT DOCUMENTS

| | | |
|---|---|---|
| CN | 102307510 A | 1/2012 |
| CN | 102401995 A | 4/2012 |
| CN | 102697445 A | 10/2012 |
| CN | 202748535 U | 2/2013 |
| CN | 103153152 A | 6/2013 |
| CN | 103211566 A | 6/2013 |
| DE | 69 05 185 U | 4/1972 |
| DE | 34 46 698 A1 | 7/1985 |
| DE | 196 27 016 C1 | 2/1998 |
| DE | 697 25 670 T2 | 7/2004 |
| DE | 101 48 099 B4 | 6/2006 |
| DE | 10 2009 060 500 | 7/2011 |
| DE | 102010034623 | 2/2012 |
| DE | 10 2012 009332 | 11/2013 |
| EP | 0 028 396 B1 | 4/1981 |
| EP | 0055394 | 7/1982 |
| EP | 1475031 | 11/2004 |
| EP | 1 759 626 A2 | 3/2007 |
| ES | 2 356 497 | 4/2011 |
| JP | S 48 27116 | 8/1973 |
| JP | S 61 118713 | 6/1986 |
| JP | S 62 227312 | 10/1987 |
| JP | H 06254049 | 9/1994 |
| JP | 10-225439 A | 8/1998 |
| JP | H11 244225 | 9/1999 |
| JP | A-2001-061772 | 3/2001 |
| JP | 2001510696 | 8/2001 |
| JP | 2002-160691 | 6/2002 |
| JP | 2002 291699 | 10/2002 |
| JP | 2003 190085 A | 7/2003 |
| JP | 2005 304 586 A | 11/2005 |
| JP | 2007 111541 A | 5/2007 |
| JP | 2007 252921 | 10/2007 |
| JP | 2007313047 | 12/2007 |
| JP | 2009 505688 A | 2/2009 |
| JP | 2009 101134 | 5/2009 |
| JP | 2009 530051 A | 8/2009 |
| JP | 2009 201762 | 9/2009 |
| JP | 2012 245058 A | 12/2012 |
| WO | WO 00/13569 A1 | 3/2000 |
| WO | WO 00/33727 | 6/2000 |
| WO | WO 2005/094665 A2 | 10/2005 |
| WO | WO 2008056642 A1 | 5/2008 |
| WO | WO 2009/008596 | 1/2009 |
| WO | 2011/114772 A1 | 9/2011 |
| WO | WO 2011/108157 A1 | 9/2011 |
| WO | WO 2013/129204 | 9/2013 |

OTHER PUBLICATIONS

International Search Report dated Oct. 8, 2014 for International Application No. PCT/EP2014/065587.
International Search Report dated Jan. 13, 2015 for International Application No. PCT/EP2014/073064.
International Search Report dated Jan. 13, 2015 for International Application No. PCT/EP2014/073066.
International Search Report dated Jan. 19, 2015 for International Application No. PCT/EP2014/073065.
Search Report for Application CN 2015800056419 in 2 pages (English Translation).
Search Report for Application CN 201480076051 in 2 pages (English Translation).
Office Action dated Sep. 4, 2017 in 7 pages For Chinese Application No. 201580005641.9.
Mar. 2, 2015 Int'l Search Report from related PCT App. No. PCT/EP2014/077938 (3 pgs).
Mar. 24, 2015 Int'l Search Report from related PCT App. No. PCT/EP2015/051252 (4 pgs).
Apr. 30, 2015 Int'l Search Report from related PCT App. No. PCT/EP2015/051245 (6 pgs).
Anonymous: "Products | BMP-TAPPI", Jun. 30, 2013 (Jun. 30, 2013), XP055394249, Gefunden im Internet: URL:https://web.archive.org/web/20130630082009/http :// www.bmp-tappi.com:80/products [gefunden am Jul. 27, 2017].

(56) References Cited

OTHER PUBLICATIONS

Anonymous: "10. Tappa per innesti rapidi femmina", Jun. 22, 2013 (Jun. 22, 2013), XP055394266, Gefunden im Internet: URL:https://web.archive.org/web/20130622161734/http:/ www.bmp-tappi.it:80/portfolio_item/tappo-per-innesti-rapidi-femmina [gefunden am Jul. 27, 2017].

* cited by examiner

SEALING COMPONENT FOR AN ENDOSCOPE CONNECTOR

CROSS REFERENCE

This application is a U.S. National Phase of PCT International Application No. PCT/EP2014/065587, filed Jul. 21, 2014 and which claims priority benefit of German Patent Application No. DE 102013214278.1 filed on Jul. 22, 2013. The entirety of each of the above-identified applications is hereby incorporated by reference.

BACKGROUND

The present invention is related to a sealing component for an endoscope plug and to an endoscope comprising such a sealing component.

A conventional endoscope is connected to an analysis unit via an endoscope cable for data connection. The endoscope cable comprises a connection plug which can be plugged and unplugged from the analysis unit.

After use endoscopes have to be cleaned. In order to clean an endoscope, the endoscope cable is unplugged from the analysis unit. Then, a sealing cap has to be placed on the connection plug to protect the connections.

PRIOR ART

Document U.S. Pat. No. 7,841,880 B2 teaches a waterproof cap for an endoscope, the waterproof cap being attached to an endoscope plug via a wire-like body.

Document EP 0 028 396 B1 teaches a cylindrical cap for an endoscope, the cylindrical cap being separate from an endoscope connection part. The cylindrical cap is a separate and single part.

Document DE 101 48 099 B4 teaches a waterproof end cap for an endoscope, the end cap being separately provided from the endoscope. The waterproof end cap is a separate and single part.

Document U.S. Pat. No. 6,547,722 B1 also teaches a waterproof end cap for an endoscope. The end cap is attached to the endoscope connection part via a wire-like body.

Document US 2002/0115907 A1 teaches an endoscope having a waterproof cap. The cap is attached to the endoscope connection part via a chain.

Thus, conventional endoscopes comprise a cap which is completely separate from the body to be sealed, or a cap connected to the body to be sealed by cable, wire, chain etc.

The cap and the chain, the cable or the wire are difficult to clean due to the presence of many undercuts. Further, the chain, the cable or the wire may tear, and the cap may get lost. Then, cleaning could not be performed any longer.

It is the object of the present invention to provide an improved sealing component for an endoscope plug, and to provide an improved endoscope.

This object is solved by a sealing component according to claim 1. An improved endoscope is shown in claim 7. Further developments are subject matter of the dependent claims.

Thus, according to the present invention, there is provided a sealing component for an endoscope plug at an end of which a plug connection end to be sealed is arranged. The sealing component comprises: a body part having a blind hole-like endoscope plug insertion opening into which the plug connection end of the endoscope plug is sealingly insertable, and a fastening portion for the fastening at an endoscope cable of the endoscope whose endoscope plug comprises the plug connection end sealingly insertable into the blind hole-like endoscope plug insertion opening.

Hence, such a sealing component can be integrated with the endoscope cable and does not get lost during the cleaning process.

The endoscope plug insertion opening of the body part can be provided with a sealing member. In this way, the plug connection end can be inserted into the endoscope plug insertion portion of the sealing component in a well-sealed manner. During the cleaning process, the sealing member ensures that no cleaning liquid reaches the connections of the plug connection end.

The body part of the sealing component can be made of resin. In this way, the body part can be produced easily and at low costs.

The fastening portion can comprise a through hole wherein the endoscope cable is slidably fastenable in the through hole. Such a sealing component is connected with the endoscope cable in a secure manner but may change its position at the endoscope cable by sliding. Thus, the sealing component may be positioned at the starting end of the endoscope cable, i.e. near a hand-held unit. When required, the sealing component may be slid to the opposite end of the endoscope cable, i.e. near the endoscope plug. The through hole can be chosen such that the sealing component is provided in a loose-fit manner at the endoscope cable. In such a case, the through hole of the sealing component has an inner diameter that is sufficiently larger than the outer diameter of the endoscope cable. In another case, the through hole can be chosen such that the sealing component is provided in a relatively firm-fit manner at the endoscope cable. In such a case, the through hole of the sealing component has an inner diameter that has approximately the same size as the outer diameter of the endoscope cable.

The fastening portion can be fastened at the endoscope cable so as to be unchangeable with respect to its position. For example, the sealing component can be cast on to the endoscope cable or can be injected-molded thereon.

The fastening portion can comprise a clamping means, wherein the clamping means is clampable to the endoscope cable. Such a clamping means ensures secure fastening of the sealing component at the endoscope cable, although the sealing component may be removed from the endoscope cable. In such a case, the sealing component can be cleaned separately. Further, a particularly fast exchange of e.g. a defective sealing component by another sealing component is possible.

Further, according to the present invention, there is provided an endoscope comprising an operation unit, an endoscope cable, an endoscope plug arranged at an end of the endoscope cable opposite to the operation unit, as well as a sealing component according to the present invention. The sealing component is arranged at the endoscope cable. A plug connection end of the endoscope plug is sealably insertable into the blind hole-like endoscope plug insertion opening of the sealing component, wherein in the inserted state, the sealing component seals the plug connection end of the endoscope plug.

The sealing component is fastened at the endoscope cable. Such an endoscope can be cleaned easily and securely since the endoscope plug is simply inserted into the sealing component provided at the endoscope cable. Since the sealing component is provided at the endoscope cable, the sealing component does not get lost during cleaning.

The sealing component can comprise a through hole at the fastening portion, wherein the endoscope cable is provided under adhesion friction in the through hole and is slidable therein. Here, the sealing component is particularly securely connected with the endoscope cable.

The fastening portion of the sealing component can be integrated at the endoscope cable. Here, the sealing component can be cast onto or injection-molded on the endoscope cable. Around the shell of the endoscope cable the shape of the sealing component is generated e.g. by a resin injection-molding process, a resin pressure die casting process, an insert moulding process, etc. Another appropriate production method by which the sealing component can be applied on the endoscope cable may also be adopted.

The fastening portion can be formed at the endoscope cable. The sealing component and the endoscope cable can consist of the same material, and can be manufactured in the same manufacturing step. In such a case, the sealing component and the endoscope cable are inseparable.

The fastening portion and the shell of the endoscope cable can be integral. In such a case, the sealing component and the endoscope cable are provided in one piece, i.e. as a unit.

The fastening portion of the sealing component can comprise a clamping means, wherein the clamping means is clamped to the endoscope cable.

The clamping means fastens the sealing component at the endoscope cable in a secure manner, wherein, when required, the sealing component could be removed from the endoscope cable. In such a case, the sealing component can be cleaned separately. Further, a particularly fast exchange of e.g. a defective sealing component by another sealing component is possible. Present endoscopes can be retrofitted with such a sealing component by clamping the new sealing component to the old endoscope cable.

At the region of the endoscope cable which adjoins the fastening portion, a bending protection means can be provided, the bending protection means preventing bending (folding) of the endoscope cable in the vicinity of the sealing component. Such a bending protection means even can for example be used in a structure in which an endoscope cable is cut open at the position where the sealing component is to be provided, and is refixed at both sides of the sealing component. In such an endoscope, the sealing component as a bending protection means can, at the proximal side and at the distal side, comprise a cylindrical or a tapering projection having such an outer dimension that the respective projection can be inserted into the respective end of the endoscope cable which results after cutting the endoscope cable.

Instead of the projection, a respective protruding cylindrical or tapering tube at a respectively predefined length can be provided at the proximal side and at the distal side of the sealing component.

As a bending protection means also a spiral spring fittingly arranged on the outer circumference of the endoscope cable can be provided, the spiral spring being anchored at the fastening portion of the sealing component respectively at the proximal side and at the distal side.

In this way, bending and folding of the endoscope cable at the transition position to the sealing component is prevented in a technically simple but effective manner.

The discussed features can be appropriately combined.

In the following, the present invention will be described in detail while referring to embodiments by means of the drawings.

Embodiment

Figure 1:
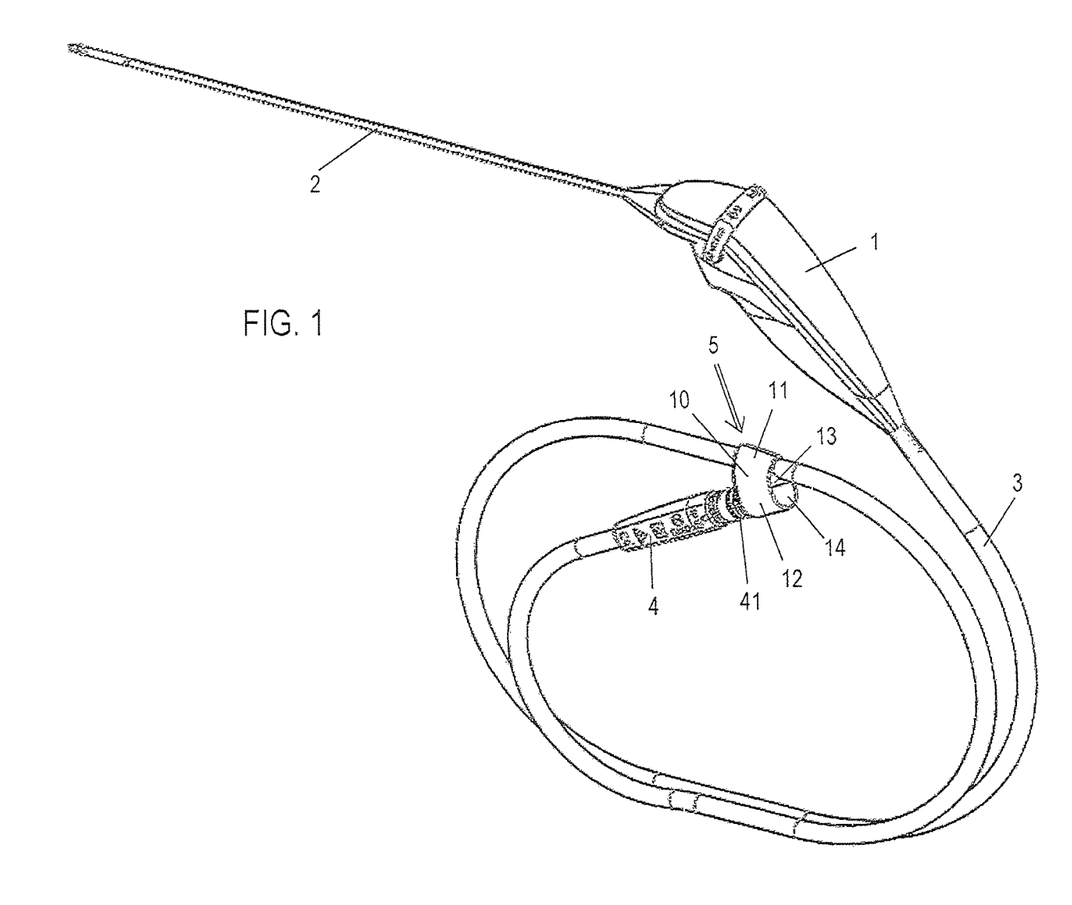
FIG. 1 shows an endoscope having a sealing component according to the present invention in a state in which an endoscope plug is inserted into the sealing component.
Figure 2:
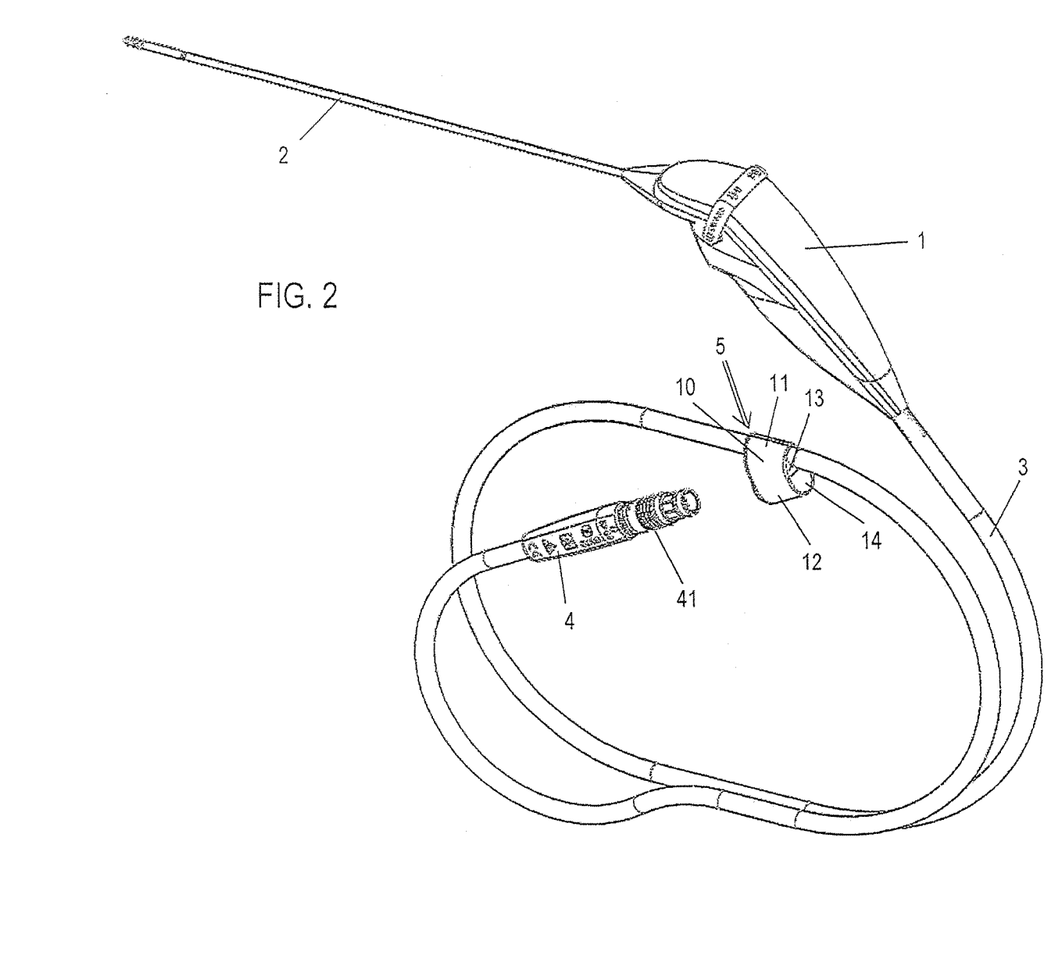
FIG. 2 shows the endoscope having the sealing component according to the present invention in a state in which an endoscope plug is taken out of the sealing component.

First of all, an embodiment according to FIGS. 1 and 2 is described.

FIG. 1 shows an endoscope having a sealing component according to the present invention in a state in which an endoscope plug is inserted into the sealing component; and FIG. 2 shows an endoscope having a sealing component according to the present invention in a state in which an endoscope plug is taken out of the sealing component.

An endoscope comprises a hand-held part 1 of an operation unit and at a distal side thereof an endoscope tube (catheter). Alternatively, at the distal side of the hand-held part 1, the endoscope can comprise an endoscope shaft instead of the endoscope tube.

At the proximal side of the hand-held part 1 of the operation unit, the endoscope comprises an endoscope cable 3 that comprises an endoscope plug 4 at the end opposite to the hand-held part 1. The endoscope plug 4 is provided with several operational switches etc. At the end of the endoscope plug 4 which is opposite to the hand-held part 1, the endoscope plug 4 comprises an electric connection 41 that can be inserted/screwed into an electronic unit/analysis unit etc. to pass on the information regarding the patient etc. gained by the endoscope to the electronic unit/analysis unit for the purpose of representation processing. In the present embodiment, the connection end 41 of the endoscope plug 4 comprises an insertion connection. Alternatively, the connection end 41 of the endoscope plug 4 can comprise a screw thread.

At its outer circumference, the endoscope cable 3 comprises an sealing component 5 in the middle of the way between the hand-held part 1 and the endoscope plug 4, as shown in FIG. 1. In the present embodiment, the sealing component 5 is provided integrally with the endoscope cable 3. Here, the sealing component 5 is injected/molded/casted at the outer circumference of the endoscope cable 3 by means of a resin injection process.

In particular, as shown in FIG. 1, the sealing component 5 comprises a body part 10 as a main element which is structured like a truncated cone. This means, the body part 10 has a truncated cone basic surface with a large diameter at the far side or left side in the view of FIG. 1, and is narrowing or tapering along the outer surface of the body part 10 in FIG. 1 toward the right side to a small circumference of the truncated cone, that is to a truncated cone cover surface with a small diameter. At this small circumference of the truncated cone, i.e. at the lower side of the truncated conical body part 10, the sealing component 5 comprises a lower bottom, i.e. the small truncated cone surface. The lower bottom has a flat ellipse-like or oval shape. The flat ellipse-like or oval shape of the lower bottom, that is the lower bottom face is separated into two portions 13 and 14 of approximately the same size. The separation line between the two portions 13 and 14 extends perpendicular to the longitudinal axis of the oval or the ellipse of the lower bottom. The first portion 13 of the lower bottom comprises an opening, and the second portion 14 of the lower bottom is completely closed.

Here, the first portion 13 of the lower bottom forms the lower opening of a through hole in the sealing component 5, through which through hole the endoscope cable extends. On the other hand, the second portion 14 of the lower bottom is filled and is positioned at the side of the body part 10 of the sealing component 5 which is opposite to an insertion opening for the endoscope plug 4 of the sealing component 5. Thus, the first portion 13 of the lower bottom forms the portion 13 of the lower bottom on the side of the endoscope cable or tube, and the second portion 14 of the lower bottom of the sealing component 5 forms the portion 14 of the lower bottom of the sealing component 5 on the side of the endoscope plug.

The body part 10 of the sealing component 5 consists of a part 11 on the side of the endoscope cable or tube, and part 12 on the side of the plug. The part 11 on the side of the endoscope tube comprises the portion 13 of the lower bottom on the side of the endoscope tube. The part 12 on the side of the plug comprises the portion 14 of the lower bottom on the side of the endoscope plug. The separation face between the part 11 on the side of the endoscope tube and the part 12 on the side of the plug extends from the separation line between the two portions 13 and 14 perpendicular to this separation line, and separates the truncated cone-shaped body part 10 into the parts 11 and 12 which have approximately the same size.

In FIG. 1, the part 11 on the side of the endoscope tube, of the sealing component 5 is arranged at the upper side, and the part 12 on the side of the plug, of the sealing component 5 is arranged at the lower side. At the side of the body part 10 of the sealing component 5, which side is opposite to the lower bottom (portions 13 and 14), i.e. at the side of the truncated cone 10 having the larger diameter, a blind hole-like endoscope plug insertion opening not shown in FIG. 1, is provided opposite to the second portion 14 of the lower bottom, the insertion connection 41 or screw connection 41 of the endoscope plug 4 being insertable into the endoscope plug insertion opening. The endoscope plug insertion opening of the sealing component 5 has such a size that the connection end 41 of the endoscope plug 4 can be inserted in an accurately fitting manner.

The through hole of the sealing component 5 for the endoscope cable 3 and the endoscope plug insertion opening at the sealing component 5 have such a positional relationship that the through hole for the endoscope cable 3 and the endoscope plug insertion opening lie in the same level and are positioned at an acute angle to each other, as is derivable from FIG. 1. Such a positional relationship brings about a construction with an advantageous insertion direction for the endoscope plug 4 since the endoscope cable 3 with the endoscope plug 4 being inserted is ensures a small overall size, and the endoscope cable 3 is in a quasi wound-up or rolled-up arrangement when the endoscope plug 4 is inserted into the sealing component 5.

At the outer circumference of the endoscope plug insertion opening a cylinder-like sealing member is assembled. This means, the outer diameter of the sealing member is arranged at the inner circumference of the endoscope plug insertion opening. The inner opening of the sealing member serves for receiving the connection end 41 of the endoscope plug 4. The sealing member consists of an appropriate sealing material such as rubber. On the other hand, the sealing component 5 is made of resin.

Except for the through hole for the endoscope cable 3 and the blind hole-like insertion opening for the connection end 41 of the endoscope plug 4, the body part 10 of the sealing component 5 is formed in a solid manner.

In the present embodiment, the body part 10 of the sealing component 5 is provided integrally at the endoscope cable 3 in such a manner that no movement of the sealing component 5 relative to the endoscope cable 3 is possible. In other words, the sealing component 5 is fixedly casted or molded onto the endoscope cable 3.

Thus, according to the present invention, the connection end 41 of the endoscope plug 4 can be inserted into the endoscope plug insertion opening of the sealing component 5 in a secure way (see FIG. 1) and can be removed therefrom again also in a secure way (see FIG. 2).

Endoscopes which hitherto do not use the sealing component 5 according to the present invention can be retrofitted with the sealing component 5. Thus, the present invention can also be applied to older endoscopes at low costs.

Figure 3:
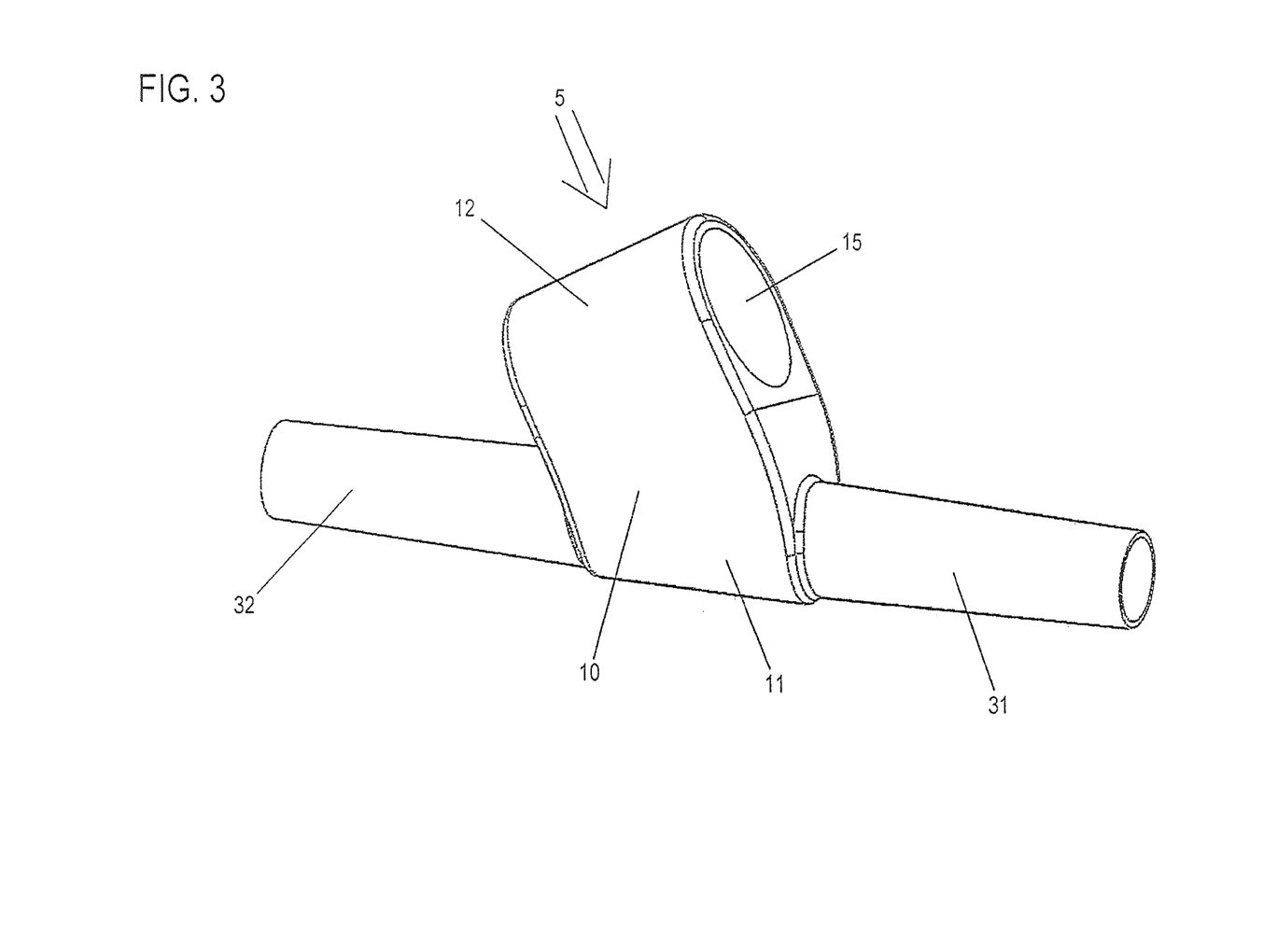
FIG. 3 shows a sealing component of a further embodiment according to the present invention without the endoscope.

FIG. 3 shows a sealing component of a further embodiment according to the present invention without an endoscope.

In this embodiment, a sealing component is provided that comprises a tapering hollow protrusion 31 at the proximal side of the part 11 of the side of the endoscope tube, of the sealing component 5 and a similar tapering hollow protrusion 32 at the distal side. The protrusions 31 and 32 have such an outer diameter that an endoscope cable can be connected thereto/attached thereupon.

Thus, in this embodiment an existing endoscope cable (not shown in FIG. 3) is cut through, and the respective protrusion 31 and 32 is inserted into the respective end of the endoscope cable which results after the endoscope cable has been cut.

In this way, a bending protection means in the region of the endoscope cable which adjoins the fastening portion, is provided, said bending protection means preventing bending (folding) the endoscope cable in the vicinity of the sealing component 5. Here, the protrusion 31 serves as a distal "tube attachment bending protection means" 31, and the protrusion 32 serves as a proximal "tube attachment bending protection means" 32. The protrusion 32 protrudes from the portion 13 on the side of the endoscope tube, of the sealing component 5.

The protrusions 31 and 32 can be glued onto or welded to the sealing component 5. Further, the protrusions 31 and 32 can also be provided integrally with the sealing component 5.

In this way, bending the endoscope cable 3 is, in a technically simple but effective way, prevented at the position where the endoscope cable 3 is mounted to the sealing component 5. The endoscope cable 3 is slid on the protrusions 31 and 32, respectively. The endoscope cable 3 can be glued thereon respectively by applying an adhesive on the protrusions 31 and 32, respectively, prior to sliding the ends of the endoscope cable 3 thereon.

Alternatives

In the embodiment discussed above, the body part 10 of the sealing component 5 is provided integrally at the endoscope cable 3. In an alternative, the through hole of the body part 10 of the sealing component 5 is designed such that the endoscope cable 3 guided therethrough can move relatively to the body part 10 of the sealing component 5 along the longitudinal direction of, the through hole of the body part 10. In other words, the endoscope cable 3 is provided in the through hole of the sealing component 5 under adhesion friction (static friction). Thus, the sealing component 5 is slidable along the endoscope cable 3 when the static friction is overcome. The coefficient of static friction, in other words the size of the through hole opening, in the sealing component 5 for the endoscope cable 3 is chosen such that, when no force is applied to the sealing component 5, the sealing component 5 maintains accuracy of position at the endoscope cable 3 without sliding along the endoscope cable 3 by itself.

In a further alternative, the through hole of the sealing component 5 can be so large that the endoscope cable 3 lies loosely in the through hole of the sealing component 5.

In a further alternative, instead of the through hole for the endoscope cable 3, the sealing component 5 possesses a clamping means by means of which the sealing component 5 is clamped fixedly to the endoscope cable 3.

In a further alternative, the diameter of the endoscope plug insertion opening can be chosen such that the connection end 41 of the endoscope plug 4 is sealingly insertable into the endoscope plug insertion opening even without a sealing member. In such a case, the sealing member of the embodiment can be omitted.

In the embodiment discussed above, the body part 10 of the sealing component 5 is formed at the endoscope cable 3 in the shape of a truncated cone. The invention is not limited to this shape. In principle, an arbitrary suitable shape can be chosen for the sealing component 5 as long as the sealing component 5 is suitably fixed to the endoscope cable 3 and the connection end 41 of the endoscope plug 4 can be securely inserted into the endoscope plug insertion opening. For instance, the sealing component 5 can be formed as a cuboid or in cylindrical shape.

In the embodiment explained above, the positional relationship between the through hole of the sealing component 5 for the endoscope cable 3 and the endoscope plug insertion opening at the sealing component 5 is chosen such that the through hole for the endoscope cable 3 and the endoscope plug insertion opening lie in the same level (same plane) and are positioned at an acute angle to each other. This positional relationship can also be chosen such that the through hole for the endoscope cable 3 and the endoscope plug insertion opening are arranged in the same plane and are aligned in parallel to each other. This positional relationship can also be chosen such that the through hole for the endoscope cable 3 and the endoscope plug insertion opening are arranged in different planes. The through hole for the endoscope cable 3 and the endoscope plug insertion opening can also be arranged at a right angle or at an obtuse angle to each other in the sealing component 5 without departing from the basic idea of the present invention.

The alternatives discussed above can be combined appropriately as long as such combinations are technically possible and conceivable.

In all embodiments, the sealing component 5 comprises a blind hole-like endoscope plug insertion opening 15. In a further alternative, the blind hole-like endoscope plug insertion opening 15 may also be covered by a respectively shaped cover cap. Such a cover cap can be designed as a plug, or such a cover cap can be designed by means of an articulated hinge, and can close the blind hole-like endoscope plug insertion opening 15 as long as the endoscope plug 4 has not been inserted, so as to protect the blind hole-like endoscope plug insertion opening 15 against contamination.

In FIG. 3, the tapering hollow protrusions 31 and 32 are provided as bending protection means at the sealing component 5. As an alternative, the protrusions 31 and 32 may be solid, i.e. not hollow. The protrusions 31 and 32 can also be provided cylindrically, but they have to comprise an outer diameter that allows slipping the endoscope cable 3 on the protrusions 31 and 32.

In a further alternative, the bending protection means at the sealing component 5 can also be provided by a distal and a proximal spiral spring in a respectively predetermined length, the spiral springs being anchored at the fastening portion of the sealing component respectively at the distal side and at the proximal side in such a manner that the spiral springs closely sit on the outer circumference of the endoscope cable.

LIST OF REFERENCE SIGNS 1 hand-held part, operation unit
2 endoscope shaft, endoscope tube (catheter)
3 endoscope cable
4 endoscope plug
5 sealing component
10 body part
11 fastening portion for attachment to the endoscope cable
12 endoscope plug insertion portion
13 first bottom portion, bottom portion on the side of the endoscope cable
14 second bottom portion, bottom portion on the insertion side of endoscope plug
15 endoscope plug insertion opening
31 distal tube attachment bending protection means
32 proximal tube attachment bending protection means
41 insertion connection, screw thread connection portion

The invention claimed is:

1. A sealing component for an endoscope plug, the endoscope plug provided at a proximal side of an endoscope cable and configured to be plugged to and unplugged from an analysis unit or an electronic unit, the endoscope plug having a plug connection end to be sealed, wherein the sealing component comprises:
   a body part having
      a blind hole-like endoscope plug insertion opening alongside the endoscope cable and configured to receive and seal the plug connection end of the endoscope plug, the blind hole-like endoscope plug insertion opening being adapted to the shape of the plug connection end, and
      a fastening portion supported by the endoscope cable, the endoscope cable having an outer circumference, the fastening portion being adapted to the shape of the outer circumference of the endoscope cable,
   wherein the blind hole-like endoscope plug insertion opening and the fastening portion are provided and formed in the body part.

2. The sealing component according to claim 1, wherein the endoscope cable is slidably fastenable in a through hole of the fastening portion.

3. The sealing component according to claim 1, wherein the fastening portion is fastenable at the endoscope cable so as to be unchangeable with respect to its position.

4. The sealing component according to claim 1, wherein the fastening portion comprises a clamping means, wherein the clamping means is clampable to the endoscope cable.

5. The sealing component according to claim 1, wherein the fastening portion comprises a bending protection means.

6. The endoscope component according to claim 1, wherein the endoscope cable and the sealing component each have a longitudinal axis, said axes being at an angle to each other.

7. The sealing component according to claim 1, wherein the sealing component is fixedly cast or molded to an endoscope cable.

8. The sealing component according to claim 1, wherein the body part is shaped to be generally that of a truncated cone.

9. The sealing component according to claim 1, wherein the sealing component is able to be disposed in the middle of the way between a hand-held part of an endoscope and the endoscope plug.

10. An endoscope comprising
an operation unit,
an endoscope cable having an exterior wall,
an endoscope plug arranged at a proximal end of the endoscope cable opposite to the operation unit and configured to be plugged to and unplugged from an analysis unit or an electronic unit, and
a sealing component for receiving the endoscope plug, the sealing component comprising:
a body part having
an endoscope plug receiving portion comprising a blind hole-like endoscope plug insertion opening configured to receive and seal a plug connection end of the endoscope plug, the blind hole-like endoscope plug insertion opening being adapted to the shape of the plug connection end, said endoscope receiving plug portion being located adjacent the exterior wall of the endoscope cable, and
a fastening portion supported by the endoscope cable, the fastening portion being adapted to the shape of an outer circumference of the endoscope cable,
wherein the blind hole-like endoscope plug insertion opening and the fastening portion are provided and formed in the body part.

11. The endoscope according to claim 10, wherein the sealing component comprises a through hole at the fastening portion, wherein the endoscope cable is provided under adhesion friction in the through hole and is slidable therein.

12. The endoscope according to claim 10, wherein the fastening portion of the sealing component is integrated at the endoscope cable.

13. The endoscope according to claim 12, wherein the fastening portion is formed at the endoscope cable.

14. The endoscope according to claim 12, wherein the fastening portion and a shell of the endoscope cable are integral.

15. The endoscope according to claim 10, wherein the fastening portion of the sealing component comprises a clamping means, wherein the clamping means is clamped to the endoscope cable.

16. The endoscope according to claim 10, wherein at the region of the endoscope cable which region adjoins the fastening portion, a bending protection means is provided, the bending protection means preventing bending of the endoscope cable in the vicinity of the sealing component.

17. The endoscope according to claim 10, wherein the body part is shaped to be generally that of a truncated cone.

18. The endoscope according to claim 10, wherein the sealing component is fixedly cast or molded to the endoscope cable.

19. The endoscope according to claim 10, wherein the sealing component is able to be disposed in the middle of the way between a hand-held part of the endoscope and the endoscope plug.

* * * * *